United States Patent [19]
Kimbrough et al.

[11] Patent Number: 4,767,048
[45] Date of Patent: Aug. 30, 1988

[54] MOBILE ROBOTIC PLATFORM

[75] Inventors: Andrew G. Kimbrough, Simi Valley; James C. Hammond, Moorpark, both of Calif.

[73] Assignee: Kinetic Energy Corp., Simi Valley, Calif.

[21] Appl. No.: 908,029

[22] Filed: Sep. 16, 1986

[51] Int. Cl.$^4$ ............................................. B23K 37/02
[52] U.S. Cl. ........................................ 228/29; 74/214; 104/165
[58] Field of Search .................... 228/7, 29; 219/60 A; 104/118–120, 165; 74/214, 215, 216

[56] References Cited

U.S. PATENT DOCUMENTS

| | | | |
|---|---|---|---|
| 2,705,629 | 4/1955 | Miller | 104/119 X |
| 3,604,612 | 9/1971 | Miller | 104/119 |
| 3,654,777 | 4/1977 | Grundman | 74/214 X |
| 3,873,798 | 3/1975 | Friedman et al. | 219/60 A |
| 3,949,618 | 4/1976 | Raschle | 74/215 |
| 4,260,869 | 4/1981 | Slavens et al. | 228/29 |
| 4,483,106 | 11/1984 | Wachs et al. | 51/241 S |
| 4,490,909 | 1/1985 | Wachs et al. | 30/97 |

FOREIGN PATENT DOCUMENTS 1194760 11/1985 U.S.S.R. ................................. 228/7

OTHER PUBLICATIONS

A publication of ARC Machines, Inc., date unknown, but acknowledged prior art.

Primary Examiner—Kenneth J. Ramsey
Attorney, Agent, or Firm—Wood, Dalton, Phillips, Mason & Rowe

[57] ABSTRACT

A mobile robotic platform and guide means therefor having a carriage with one or more uniquely constructed drive rollers having radially-extending metal filaments embedded in a complaint material and which coact with a track defining the guide means which has a length of textured material, such as wire mesh secured thereto. The coaction provides an infinite pitch rack drive. The mobile robotic platform can have the carriage thereof provided with two or more tractor units pivotally mounted thereto and each of which carry a pair of the aforesaid drive rollers whereby the carriage can follow guide means of varying contours with controlled travel and continuous operation of an operative device carried by the carriage.

14 Claims, 2 Drawing Sheets

U.S. Patent  Aug. 30, 1988  Sheet 1 of 2  4,767,048
FIG. 1
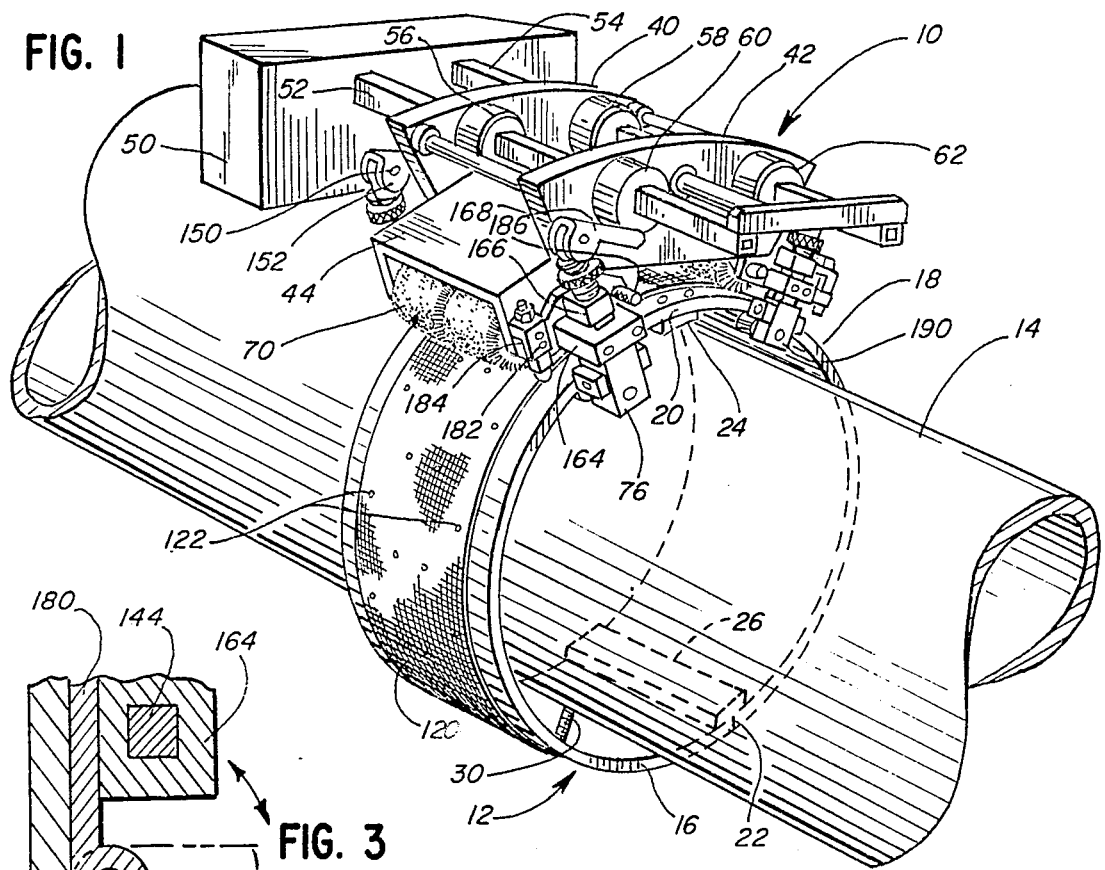
FIG. 3
FIG. 2
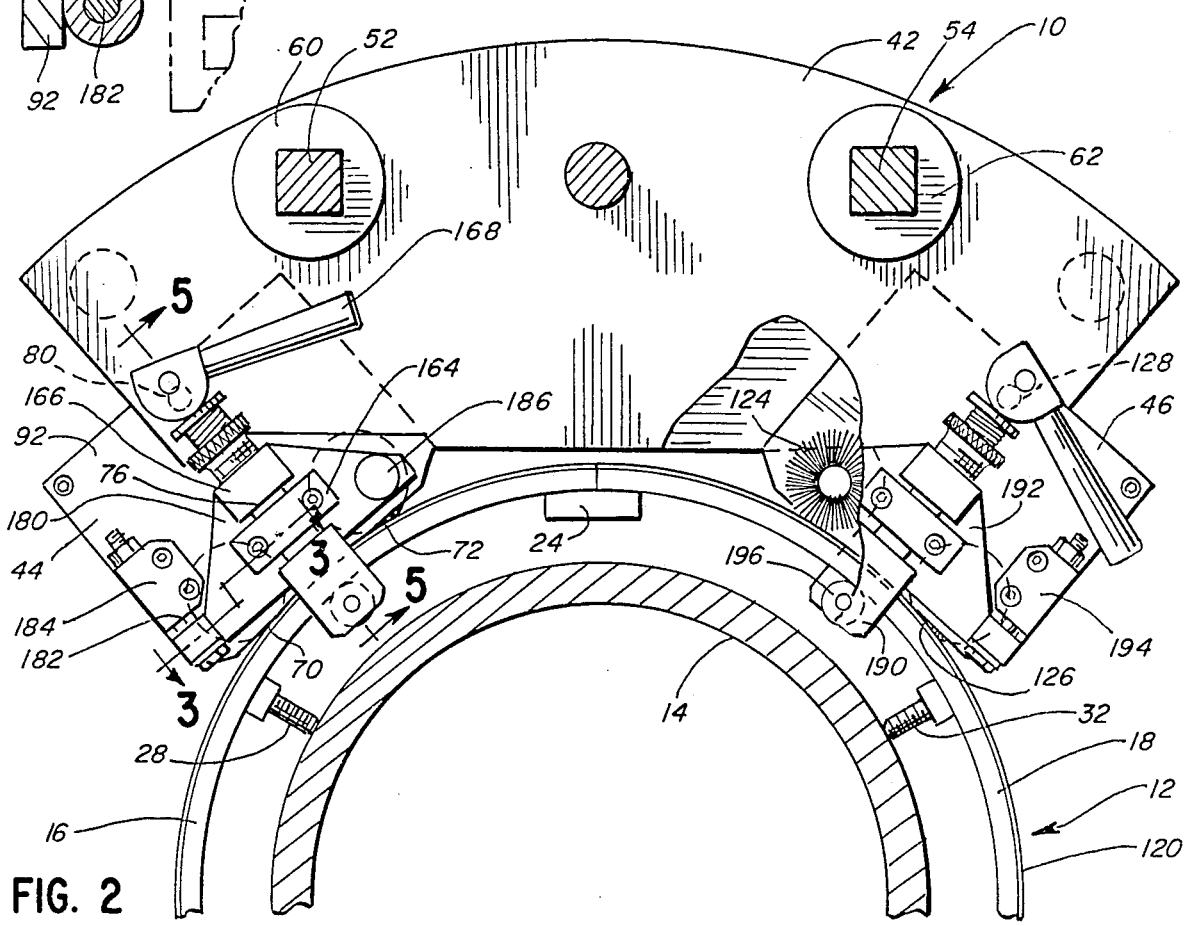

MOBILE ROBOTIC PLATFORM

BACKGROUND OF THE INVENTION

This invention pertains to a mobile robotic platform operable in association with guide means mountable on a member for transporting an operative device relative to the member. More particularly, the mobile robotic platform has a travelling carriage which can mount any desired operative device, with examples of such devices being ultrasonic testing equipment, X-ray machines and welding equipment. Structure associated with the carriage and the guide means provides for accurately controlled travel of the carriage and with the control having a remote capability.

DESCRIPTION OF THE PRIOR ART

One use of the disclosed mobile robotic platform is to carry a weld torch and other mechanisms around the circumference of a pipe.

Several different systems are known for movably mounting a carriage on a pipe and for moving the carriage around the pipe.

One of these systems embodies the use of one or more chains wrapped around a pipe and a carriage has one or more driven sprockets which engage with the chain and, as the sprockets are rotated, the carriage is caused to move along the chain and around the pipe. Systems of this type are shown in the Wachs et al. U.S. Pat. Nos. 4,483,106 and 4,490,909.

A second system is of a type shown in U.S. Pat. No. 3,873,798 wherein a carriage has friction drive rollers that are loaded against a knurled track surface of a mounting track by a track-follower roller rolling against an undercut surface on the inside of the track. A primary disadvantage of this system is the excessive loading force required to maintain adequate traction between the friction drive rollers and the knurled track surface to insure constant travel speed. The use of excessive loading force results in poor drive efficieny and excessive wear of the friction drive rollers and the track.

A third system has a carriage movable along a track, with the track having rack gears cut in the track surface which are engaged by one or more drive pinions supported by the carriage. Rollers of various configurations or cam followers are used to hold the drive pinions against the rack. This system provides an efficient drive configuration. However, the cost and lead times to fabricate tracks of relatively large diameter having the rack gears cut in the surface thereof is excessive.

The invention disclosed herein distinguishes over the foregoing systems in utilizing a low-cost drive configuration having unique components which coact to provide an infinite pitch gear drive with excellent drive efficiency and without excessive loading of the components to minimize wear of the components.

SUMMARY OF THE INVENTION

A primary feature of the invention is to provide a mobile robotic platform having a carriage with one or more drive rollers and which is associated with guide means in the form of a track and with excellent drive efficiency being achieved by means of gear-type drive achieved without the cutting of gear teeth on the track supporting the carriage and with constant travel speed being assured by adequate traction being maintained without excessive loading force between the drive roller and the track.

A further feature of the invention, is the versatility of the structure in that the carriage can be guided by a track or tracks which can be made with a transition from a convex contour to a concave contour with an intermediate straight section, or variations thereof, without stopping a process being performed by equipment mounted on the carriage.

More particularly, the invention embodies a drive roller for the carriage constructed of radially-extending metal filaments embedded in a compliant material and which coact with a track having textured material secured to the outside surface thereof.

The drive roller is compressively loaded against the textured material to assure an engagement between the ends of the metal filaments and the textured material for effectively defining a geared relation therebetween.

Additionally, the carriage of the mobile robotic platform has two or more spaced-apart tractor units, each having a pair of the drive rollers, with the tractor units being pivotally mounted to the carriage to adjustably mount the carriage to a track having any one of many different contours. The drive rollers are compressively loaded against the track by guide units coacting with the track for guiding the carriage and achieving the compressive loading. The guide units have means to adjust the degree of loading and with there being a guide unit at each end of each of the tractor units, the guide units at one end of the tractor units are hinged to facilitate placement and removal of the carriage relative to the track.

In a specific embodiment, the drive rollers are formed from a stack of circular wire brushes having radial bristles and which are potted in a compliant material, such as urethane, to hold the bristles perpendicular to the track surface. Under compressive loading, the ends of the bristles are sufficiently exposed to engage the textured material and, more particularly, to engage segments of a woven wire mesh screen, defining the textured material, and which extends along the track and is secured thereto.

The mobile robotic platform embodying the invention and as described in the preceding paragraphs offers a number of advantages over prior known drive systems, including the maintenance of adequate traction between a drive roller and a track, without excessive loading therebetween to reduce wear on the components; significant component fabrication savings and lead time reductions as a result of merely attaching textured material, such as wire screen to a simple track of the desired contour without having to cut gear teeth on the track; and the carriage can be continuously moved along the track, even though the track may be of varying contour, including convex, concave and straight sections.

An object of the invention is to provide a new and improved mobile robotic platform and guide means associated therewith providing new and improved results not heretofore known in the art.

A further object of the invention is to provide a mobile robotic platform and guide means therefor including a carriage having at least one drive unit mounted thereon, said drive unit having a drive roller and a motor for rotating the drive roller and said guide means comprising a track mountable to a member and shaped to define a path of travel of the carriage relative to said member, the improvement comprising: a length of textured material extending lengthwise of the track and secured thereto; and said drive roller being comprised of a plurality of radially-extending metal filaments embedded in a compliant material.

Still another object is to provide a mobile robotic platform having a carriage for support of welding components or the like, a track mounting the carriage for movement relative to a member on which an operation is to be performed, and means on the carriage for guiding and propelling the carriage relative to the track comprising at least one tractor unit, and means pivotally mounting the tractor unit on the carriage, said tractor unit having a drive roller for rolling engagement with the track, and a drive motor on the tractor unit for driving the drive roller, said track having a layer of mesh material secured thereto and the drive roller having radial wire bristles embedded therein and extending to the surface of the drive roller.

Still another object of the invention is to provide a mobile robotic platform having a carriage for support of at least one operative component, a track mounting the carriage for movement relative to a member on which an operation is to be performed by said component, and means on the carriage for guiding and propelling the carriage relative to the track comprising two or more spaced-apart tractor units, means pivotally mounting the tractor units individually to the carriage, said tractor units each having a pair of drive rollers for rolling engagement with the track, a pair of adjustable guide units one at each end thereof for engaging the edges and inner side of the track including a compressively-loaded member engaging the inner side of the track for loading the drive rollers against the track, and a pair of drive motors one on each tractor unit for driving the drive rollers.

Still another object of the invention is to provide a welding machine and guide means therefor including a welding carriage having at least one drive unit mounted thereon, said drive unit having a drive roller and a motor for rotating the drive roller and said guide means comprising a track mountable to a member such as a pipe or the like and shaped to define a path of travel of the welding carriage relative to said member, the improvement comprising: a length of textured material extending lengthwise of the track and secured thereto; and said drive roller being comprised of a plurality of radially-extending metal filaments embedded in a compliant material and having their ends exposed to the surface of the drive roller.

A further object of the invention is to provide a welding machine and guide means as described in the preceding paragraph wherein said compliant material is a polyurethane material which holds the metal filaments perpendicular to the track and the textured material is a woven wire mesh fastened to the track.

BRIEF DESCRIPTION OF THE DRAWINGS

FIG. 1 is a perspective view of the mobile robotic platform, looking toward the rear thereof, and the guide means therefor and shown in association with a pipe;

FIG. 2 is a rear elevational view of the mobile robotic platform and guide means, with parts broken away and shown mounted on a pipe;

FIG. 3 is a fragmentary section, taken generally along the line 3—3 in FIG. 2;

DESCRIPTION OF THE PREFERRED EMBODIMENT

Figure 4:
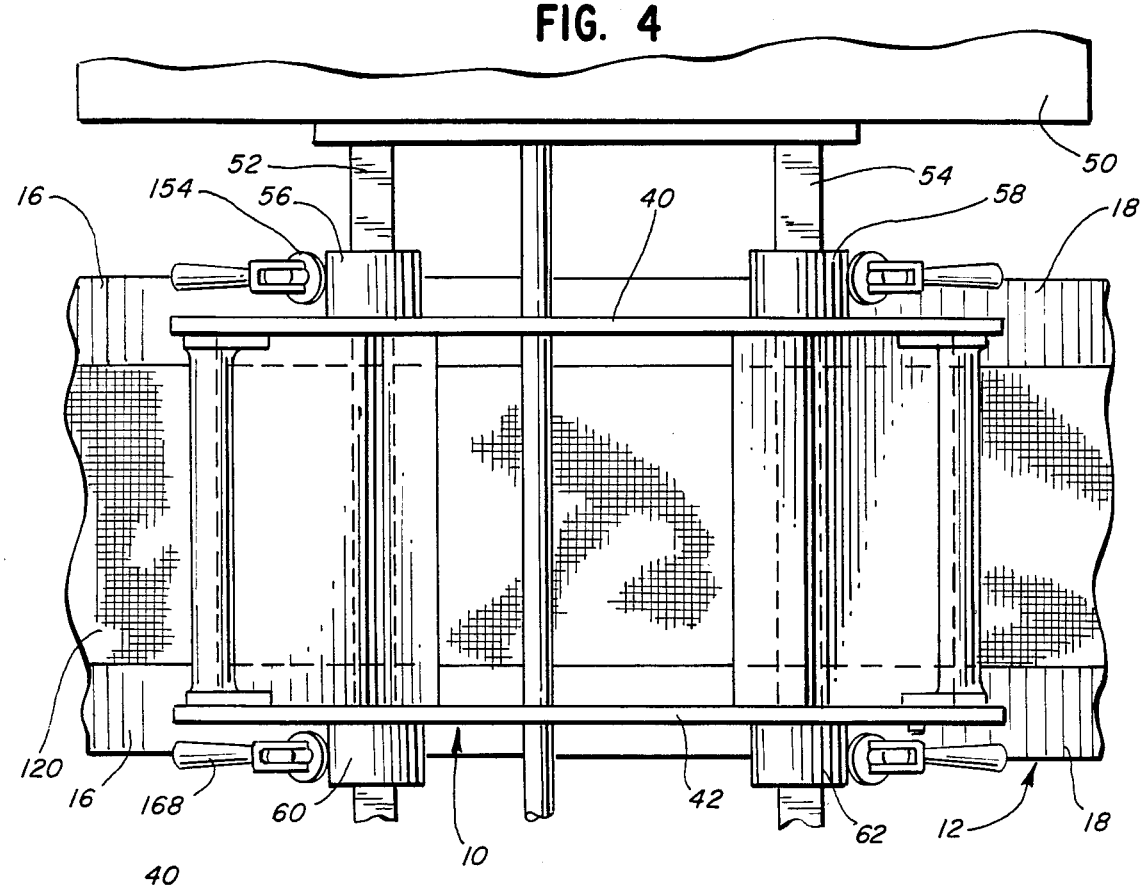
FIG. 4 is a fragmentary plan view of the mobile robotic platform and the guide means thereof.

The mobile robotic platform is indicated generally at 10 and is mounted on guide means, indicated generally at 12. The structure is shown in FIGS. 1 and 2 in association with a length of pipe 14.

The guide means 12 is constructed from a pair of metal track plates 16 and 18, preferably of rolled aluminum which are each of semicircular configuration and assembled in end-to-end relation to define a circular track. As seen in FIGS. 1 and 2, the semicircular track plates 16 and 18 abut at 20,-22, respectively. These track plates are held in assembled relation by a pair of elongate attaching plates 24 and 26 which underlie the inner surface of the track and which are attached to the track plates by threaded members extending through openings in the track plates and threaded into the attachment plates. The track plates have adjustable locating screws, positioned at three equally arcuately spaced locations, with there being a row of the adjusting screws extending for the width of the track at each location to facilitate concentric mounting of the track relative to the pipe. The track plate 16 has a row of adjusting screws 28 at one location and a second row of adjusting screws 30 at another location, with a third set of adjusting screws 32 being carried by the track plate 18.

The mobile robotic platform 10 has a carriage defined by a pair of rigidly interconnected spaced-apart plates 40 and 42 which carry an operative device and pivotally mount a pair of tractor units 44 and 46.

An operative device is shown diagrammatically at 50, and such device can be whatever equipment is needed to perform an operation on a member or to perform a testing function, as examples. The operative device 50 can be carried around the pipe by movement of the mobile robotic platform 10 along the guide means 12 and can also have additional movements, such as movement back and forth relative to the mobile robotic platform, with such movement being provided by mounting of the operative device 50 on a pair of elongate bars 52 and 54 which are movably mounted in a pair of bearings 56 and 58 on the carriage plate 40 and a pair of bearings 60 and 62 on the carriage plate 42. A suitable motor drive (not shown) can be used to effect movement of the bars 52 and 54 and the operative device 50.

Figure 5:
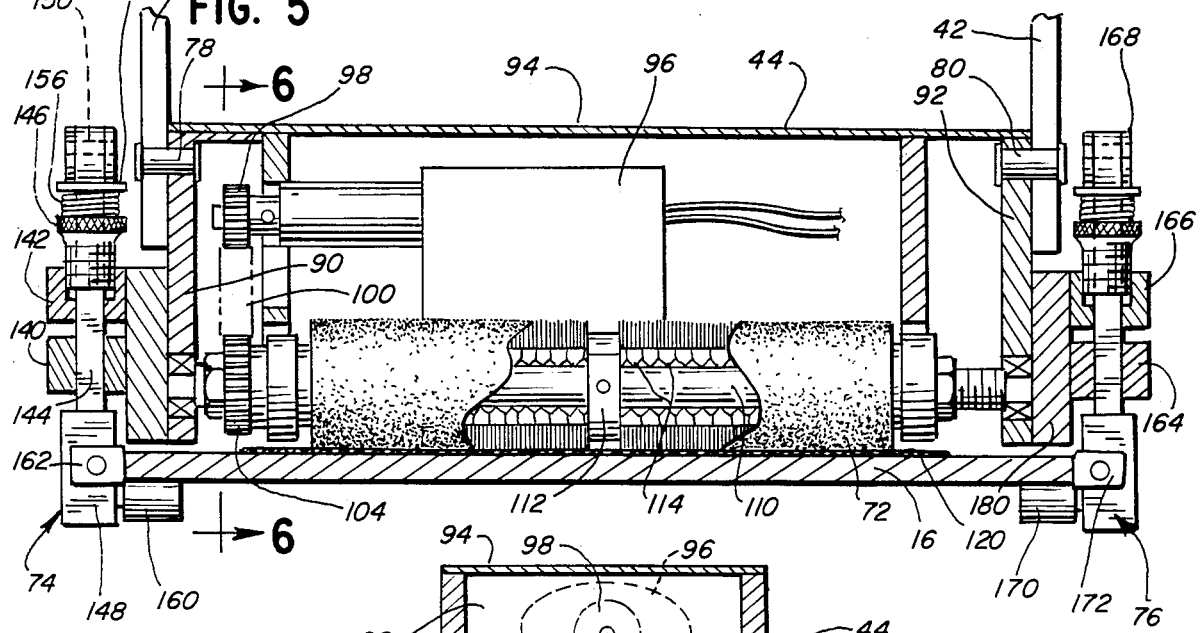
FIG. 5 is a sectional view, on an enlarged scale taken generally along the line 5—5 in FIG. 2 and showing a part of the mobile robotic platform in association with the guide means.
Figure 6:
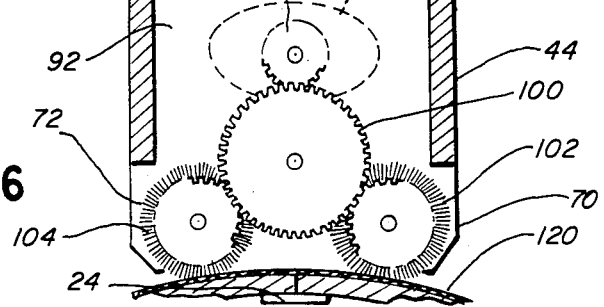
FIG. 6 is a sectional view, taken generally along the line 6—6 in FIG. 5.

Each of the tractor units 44 and 46 is of the same construction and mounted similarly to the carriage, with the tractor unit 44 being shown in detail in FIG. 5 and 6. The tractor unit 44 has a pair of rotatably-mounted drive rollers 70 and 72 and a pair of similarly-constructed guide units 74 and 76 positioned at opposite ends thereof. The tractor unit 44 is pivotally mounted to the carriage plates 40 and 42 by a pair of pivot pins 78 and 80, with the pivot being located along a line normal to a line between the rotational axes of the drive rollers 70 and 72. The tractor unit 44 may assume different pivotal positions relative to the carriage to accommodate mounting of the mobile robotic platform to guide means of varying contours, including substantially different diameters.

The drive rollers 70 and 72 are rotatably mounted between end plates 90 and 92 of the tractor unit 44 having a connecting top plate 94 and with the end plates 90 and 92 pivotally mounting the pivot pins 78 and 80. Each of the drive rollers has reduced diameter shaft ends, which are rotatably supported within bearings carried by the end plates.

The tractor unit has an electrical drive motor 96 having an output shaft with a gear 98 which meshes with an idler gear 100. The idler gear 100 meshes with a gear 102 on the drive roller 70 and a gear 104 on the drive roller 72. Operation of the motor 96 results in rotation of the drive rollers 70 and 72, with resulting movement of the carriage of the mobile robotic platform along the guide means 12. The drive rollers 70 and 72 are uniquely constructed and in association with textured material secured to the track plates provide an infinite pitch rack drive for the tractor unit. Referring particularly to FIG. 5, and the showing of drive roller 72 therein, the drive roller has a shaft 110 with a central collar 112. A series of circular radial bristle wire brushes 114 having central openings are stacked on the shaft 110 to either side of the collar 112 and are bonded together in a compliant material. An example of such compliant material is a urethane compound, more particularly FLEXANE 80 offered by Devcon. The stacked wire brushes are potted in the compliant material and the wire bristles extend to the surface of the drive roller. This structure defines a plurality of radially-extending metal filaments which extend perpendicular to the surface of the track. It will be recognized that it is within the scope of the invention to utilize structure other than commercially-available circular radial bristle wire brushes to achieve the metal filament construction.

The drive rollers coact with a length 120 of textured material extending around the surface of the guide means and for substantially the entire width of the track plates, as seen in FIGS. 1 and 5. This textured material coacts with the compressively loaded drive rollers to define a geared relation therebetween and provide a positive traction drive. The textured material can be a woven mesh material and, more particularly, a woven wire mesh which is secured to the track plates 16 and 18 in a suitable manner, as by rivets 122.

The tractor unit 46 is of the same construction as the tractor unit 92 and has a pair of drive rollers 124 and 126 of the same construction as the drive roller 72 and with the drive therof being from a motor and through gearing similar to that shown in FIG. 6 for tractor unit 44. Tractor unit 46 is pivoted to the carriage plates 40 and 42 by pivot pins, one of which is indicated at 128.

The guide units 74 and 76 for the tractor unit 44 are of the same basic construction. One of the guide units is mounted for pivotal movement to facilitate mounting of the mobile robotic platform to the guide means, while the other is fixed to the tractor unit. Referring to the guide unit 74, a pair of blocks 140 and 142 are fixed to the end plate 90 of the tractor unit, with the block 40 having a square hole to movably guide a square rod 144 and the block 142 having a threaded recess, as well as an opening for the rod 144. An externally-threaded tubular member 146 threads into the block 142. The square rod 144 carries a block 148 at its lower end and, at its upper end, pivotally mounts at 150 a handle having a cam surface 152 which coacts with a washer 154, with a spring 156 between the washer 154 and the externally-threaded tubular member 146. The block 148 has an inwardly-extending roller 160 which underlies the undersurface of the track plates and mounts a Teflon block 162 which rides against an edge of the track plates. The guide unit 76 is of a similar construction having the fixed blocks 164 and 166 and the handle 168 and with the inwardly-extending roller 170 and a Teflon block 172 engaging an edge of the track plates. With the handles of the guide units in the positions shown in the drawings, the drive rollers 70 and 72 are compressively-loaded against the length 120 of textured material, by drawing the rollers 160 and 170 compressively against the underside of the track plates through the action of compressing the springs 156 of the guide units. When this compressive engagement is to be released, the handles are pivoted upwardly to remove the cam surface from coaction with the washer 154 and release the spring force which enables lowering of the rollers 160 and 170 from compressive engagement with the underside of the track plates.

The guide unit 76 is pivotally mounted by having a plate 180 mounting the blocks 164 and 166 pivotally mounted to the tractor end plate 92. This pivot mounting is achieved by mounting of the plate 180 by a pivot pin 182 in a block 184 fixed to the tractor end plate 92 and with the plate 180 being releaseably-retained in operative position by a threaded member 186 carried by the mounting plate 180 and threadable into the tractor end plate 92.

The tractor unit 46 has a similar pair of guide units, with a guide unit 190 being pivotally mounted, similar to the guide unit 76 by pivoting of a plate 192 pivotally mounted to a block 194 and with a roller 196 engageable with the underside of the track plates. There is also a guide unit at the opposite end of the tractor unit 46, similar to the guide unit 74.

With the guide units 76 and 190 operated to a release position by upward pivoting of their handles, the guide rollers 170 and 196 are out of compressive engagement with the underside of the track plates and these guide units can then be swung outwardly on their pivots to a location wherein the mobile robotic platform may be removed from the guide means by movement toward the left, as viewed in FIG. 1. The components can be reassembled by movement toward the right in FIG. 1 and then pivoting the guide units 76 and 190 back to the position shown in FIG. 1, followed by operation of the guide unit handles to establish the compressive loading of the tractor unit drive rollers against the textured material.

The operation may be seen when viewing the mobile robotic platform in FIGS. 1 and 2. The compressive loading achieved by lowering of the handles of the guide units places the drive rollers in compressive engagement with the textured material secured to the track plates. With the drive rollers having the radially-extending metal filaments held in the compliant or compressive material, there is good exposure of the end thereof to interfit with the textured material and provide an effectively positive gear drive for controlled travel of the mobile robotic platform along the guide means. With the pair of tractor units 44 and 46, the mobile robotic platform has the capability of operating to follow differing contours, such as guide means having concave and convex sections, as well as straight sections and, at all times, the effectively positive gear drive is maintained. Adequate traction is maintained without excessive compressive loading. Any shape guide means may be readily achieved by merely shaping the plate or plates defining the guide means and securing the textured material, such as wire mesh, thereto with resulting substantial cost and time savings.

There are many different applications for the mobile robotic platform and the showing thereof in the drawings in association with the pipe is only for illustrative purposes. The operative device 50 carried by the mobile robotic platform can be any device required for a particular operation that is to be performed. The operation can be either testing, as by ultrasonic means or X-ray, or the operative device can be structure for performing operations on a member, such as a pipe, with one such operation being welding.

We claim:

1. A mobile robotic platform and guide means therefor including a carriage having at least one drive unit mounted thereon, said drive unit having a drive roller and a motor for rotating the drive roller and said guide means comprising a track mountable to a member and shaped to define a path of travel of the carriage relative to said member, the improvement comprising: a length of textured material extending lengthwise of the track and secured thereto; and said drive roller being comprised of a plurality of radially extending metal filaments embedded in a compliant material.

2. A mobile robotic platform and guide means as defined in claim 1 wherein said compliant material is a polyurethane material.

3. A mobile robotic platform and guide means as defined in claim 1 wherein said textured material is woven wire mesh.

4. A mobile robotic platform as defined in claim 3 wherein said woven wire mesh is riveted to said track.

5. A mobile robotic platform as defined in claim 1 wherein a plurality of circular radial bristle wire brushes are embedded in said compliant material to define said radially extending metal filaments.

6. A mobile robotic platform as defined in claim 5 wherein, in operation, said metal filaments extend beyond the surface of said drive roller to mesh with said textured material.

7. A mobile robotic platform having a carriage for support of welding components or the like, a track mounting the carriage for movement relative to a member on which an operation is to be performed, and means on the carriage for guiding and propelling the carriage relative to the track comprising at least one tractor unit, and means pivotally mounting the tractor unit on the carriage, said tractor unit having a drive roller for rolling engagement with the track, and a drive motor on the tractor unit for driving the drive roller, said track having a layer of mesh material secured thereto and the drive roller having radial wire bristles embedded therein and extending to the surface of the drive roller.

8. A travelling machine for welding or the like and guide means therefor including a carriage having at least one drive unit mounted thereon, said drive unit having a drive roller and a motor for rotating the drive roller and said guide means comprising a track shaped to define a path of travel of the carriage, the improvement comprising: a length of material textured in a repetitive pattern extending lengthwise of the track and secured thereto; said drive roller being comprised of a plurality of radial filaments embedded in a compressible material; and means for bringing said drive roller and textured material into compressive engagement.

9. A mobile robotic platform having a carriage for support of at least one operative component, a track mounting the carriage for movement relative to a member on which an operation is to be performed by said component and having an inner side spaced from the member, and means on the carriage for guiding and propelling the carriage relative to the track comprising two or more spaced-apart tractor units, means pivotally mounting the tractor units individually to the carriage with the tractor units free to pivot during movement along the track, said tractor units each having a pair of drive rollers for rolling engagement with the track and which are spaced apart a sufficient distance to provide independent mechanical stability for a tractor unit, a pair of adjustable guide units one at each side of a tractor unit for engaging the edges and inner side of the track including a compressively-loaded member intermediate the driver rollers and engaging the inner side of the track for loading the drive rollers against the track, and a pair of drive motors one on each tractor unit, means for driving a plurality of the drive rollers, each of said drive rollers being formed of radial wire bristles embedded in a compliant material, and said track having a wire mesh material extending lengthwise thereof and secured thereto for coaction with the ends of said radial wire bristles.

10. A mobile robotic platform and guide means therefor including a carriage having at least one drive unit mounted thereon, said drive unit having a drive roller and a motor for rotating the drive roller and said guide means comprising a track shaped to define a path of travel of the carriage, the improvement comprising: a length of woven mesh material extending lengthwise of the track and secured thereto; said drive roller being comprised of a plurality of circular radial bristle wire brushes embedded in a compressible material; and means for bringing said drive roller and woven mesh material into compressive engagement.

11. A welding machine and guide means therefor including a welding carriage having at least one drive unit mounted thereon, said drive unit having a drive roller and a motor for rotating the drive roller and said guide means comprising a track mountable to a member such as a pipe or the like and shaped to define a path of travel of the welding carriage relative to said member, the improvement comprising; a length of textured material extending lengthwise of the track and secured thereto; and said drive roller being comprised of a plurality of radially-extending metal filaments embedded in a compliant material and having their ends exposed to the surface of the drive roller.

12. A welding machine and guide means as defined in claim 11 wherein said compliant material is a polyurethane material which holds the metal filaments perpendicular to the track.

13. A welding machine and guide means as defined in claim 11 wherein said textured material is a woven wire mesh fastened to said track.

14. A drive system for a carriage which has apparatus mounted thereon for performing operations on a member with the carriage being movable relative to the member, comprising: a track spaced from and fixed to the member; at least a pair of spaced-apart tractor units pivotally mounted on the carriage; means on the ends of each of the tractor units for engaging the edges of the track to guide the carriage relative to the track; a pair of drive rollers rotatably mounted on each tractor unit and having radial metal elements exposed at the surface thereof carried by a compliant material; means for loading said drive rollers against the track including a compressively-loaded member engaging the inner side of the track; and a length of mesh material fixed to the exterior of the track with which the metal elements mesh to provide positive traction between the drive rollers and the track.

* * * * *